United States Patent [19]

Konrad et al.

[11] Patent Number: 4,661,114
[45] Date of Patent: Apr. 28, 1987

[54] 3-AMINO-5-HYDROXYPYRIDINE DERIVATIVES AND HAIR COLORING COMPOSITIONS CONTAINING THE SAME

[75] Inventors: Eugen Konrad, Darmstadt; Thomas Clausen, Alsbach, both of Fed. Rep. of Germany

[73] Assignee: Wella Aktiengesellschaft, Darmstadt, Fed. Rep. of Germany

[21] Appl. No.: 798,018

[22] Filed: Nov. 14, 1985

[30] Foreign Application Priority Data

Nov. 17, 1984 [DE] Fed. Rep. of Germany ....... 3442128

[51] Int. Cl.$^4$ ..................... A61K 31/40; C07D 213/72
[52] U.S. Cl. ........................................ 8/409; 546/296; 8/423; 8/406
[58] Field of Search ..................... 546/296; 8/406, 409, 8/423

[56] References Cited

U.S. PATENT DOCUMENTS 3,630,847 12/1971 Rey et al. ............................. 546/296
4,452,603 6/1984 Konrad et al. ...................... 546/296
4,473,375 9/1984 Clausen ............................... 546/296

FOREIGN PATENT DOCUMENTS 3132885 3/1983 Fed. Rep. of Germany ...... 546/296

OTHER PUBLICATIONS

Colour Index, Third Edition, vol. 4, Published by The Society of Dyers and Colourists, pp. 4053, 4070, 4389, 4534, 4537.

C. D. Johnson et al., J. Chem. Soc. (B), 1967, pp. 1204–1210.
T. Cohen et al., J. Org. Chem. vol. 42, No. 12, (1977), pp. 2053–2058.
Information regarding TA 1535, TA 1537, TA 1538, TA 98 and TA 100 cited on p. 12 of the specification.

Primary Examiner—Henry R. Jiles
Assistant Examiner—J. Richter
Attorney, Agent, or Firm—Michael J. Striker

[57] ABSTRACT

New 3-amino-5-hydroxypyridine derivatives are disclosed, of the formula I

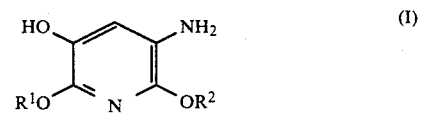

wherein $R^1$ and $R^2$ are independently $CH_3$, $C_2H_5$ or $C_2H_4OH$, and its physiologically compatible salts, as well as oxidation hair coloring compositions based upon the compounds of general formula I as coupler substance. The oxidation hair coloring compositions based upon the new couplers, of which the 3-amino-5-hydroxy-2,6-dimethoxypyridine is preferred, are particularly suitable in combination with known developer substances to obtaining red, red-brown, bond and orange colored tones. The new coupler substances of formula I prove to have favorable toxicological and dermatological characteristics.

12 Claims, No Drawings

3-AMINO-5-HYDROXYPYRIDINE DERIVATIVES AND HAIR COLORING COMPOSITIONS CONTAINING THE SAME

BACKGROUND OF THE INVENTION

The present invention concerns new 3-amino-5-hydroxypyridine derivatives, as well as compositions for the oxidative coloration of hair, based upon developer and coupler substances, wherein the new 3-amino-5-hyroxypyridine derivatives are employed as coupler substance.

Oxidation dyes have developed an essential significance for hair coloration. The coloration is produced with this class of dyes by means of reaction with determined developer substances with determined coupler substances, in the presence of a suitable oxidation agent.

As developer substances, preferably 2,5-diaminotoluene, 4-aminophenol and 1,4-diaminobenzene have been employed, however also 2,5-diaminoanisol, 2,5-diaminobenzylalcohol and 2-($\beta$-hydroxyethyl)-1,4-diaminobenzene have acquired a certain significance. In certain cases, also tetraaminopyridine can be employed as developer substance. The preferably employed coupler substances are m-phenylendiamine and its derivatives, 2,4-diaminoanisol and 2,4-diaminophenetol, resorcin, 4-chlorresorcin, 1-naphthol, m-aminophenol and 5-amino-o-cresol. The last-mentioned compounds, on account of their ability to provide red tones after oxidative coupling with 1,4-diaminobenzene or 1,4-diaminobenzene derivatives, acquired significance as coupler for the nuancing of natural and so-called mod tones.

Numerous particular requirements are placed on oxidation dyes that are supposed to be employed for the coloring of human hair. Thus, they must be harmless both from a toxicological and dermatological point of view, and make possible the obtaining of colorings of the desired intensity. Moreover, it is necessary that a broad palette of different color nuances can be obtained through a combination of suitable developer and coupler components. Additional requirements for the obtainable hair colorations are a good fastness to light, permanent waving, acid and rubbing. In each case, however, such hair colorations must remain stable, i.e., without influence of light, chemical means or rubbing over a time period of at least 4-6 weeks.

M-aminophenol, employed for some time in hair dyes as a red coupler, its derivatives as well as 5-amino-o-cresol, as well as the likewise employed 1-naphthol, cannot, however, satisfactorily fulfill all of the above requirements.

SUMMARY OF THE INVENTION

It is, therefore, an object according to the present invention to make available, oxidation hair dyes based upon such coupler substances, with which the art-recognized requirements can be better fulfilled.

It has now been discovered that compositions for the oxidative dyeing of hair, based upon a developer substance-coupler substance-combination, thereby characterized in that they contain as coupler substance a 3-amino-5-hydroxypyridine derivative of the general formula I

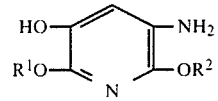

(I)

whereby $R^1$ and $R^2$ are the same or different and are each $CH_3$, $C_2H_5$ or $C_2H_4OH$, also in the form of the physiologically compatible salts, satisfy the inventive object to an outstanding extent.

The 3-amino-5-hydroxypyridine derivative of the given formula I, such as e.g., 3-amino-5-hydroxy-2,6-dimethoxypyridine and 3-amino-5-hydroxy-2,6-di-(2'-hydroxyethloxy)-pyridine contained as coupler substances in the hair dyeing compositions according to the present invention are well soluble in water. They display, moreover, an excellent storage stability, particularly as components of the herein hair coloring compositions.

The coupler substances according to the present invention, of which 3-amino-5-hydroxy-2,6-dimethoxypyridine is preferred, should be contained in the hair coloring compositions in a concentration from about 0.01 up to 3.0 percent by weight, preferably 0.1 up to 2.0 percent by weight. The coupler substances of formula I should be employed in the hair coloring compositions either as free base or in the form of their physiologically compatible salts with organic or inorganic acids, e.g., chloride, sulphate, phosphate, acetate, propionate, lactate or citrate. Moreover, they can be provided as phenolate in strongly alkaline medium. Regardless of the fact that the advantageous characteristics of the herein described new coupler substances suggest that they be employed as sole couplers, it is obviously also possible to employ the new coupler substances of formula I together with known coupler substances.

Of the known coupler substances coming into consideration as components of the herein described hair coloring compositions, mention may be made by way of example of resorcin, 4-chlororesorcin, 4,6-dichlororesorcin, 2-methylresorcin, 2-amino-4-(2'-hydroxyethylamino)-anisol, 2,4-diaminobenzyl alcohol, 2,4-diaminophenylethanol, m-phenylenediamine, 5-amino-2-methyl-phenol, 2,4-diaminoanisol, 2,4-diaminophenoxyethanol, 4-amino-2-hydroxyphenoxyethanol, 1,5-dihydroxytetralin, 1-naphthol, m-aminophenol, 3-amino-2-methylphenol, 5-amino-2-methyl-phenol, 4-hydroxy-1,2-methylenedioxy-benzene, 4-amino-1,2-methylenedioxybenzene, 4-(2'-hydroxyethylamino)-1,2-methylenedioxybenzene, 2,4-diaminophenol and 4-hydroxyindol. It can, furthermore, be advantageous, for the provision of determined nuances, to combine with other heterocyclical couplers, such as for example the 3,5-diamino-2,6-dimethoxypyridine or the 3,5-diamino-2,6-di(2'-hydroxyethyloxypyridine, described in DE-OS No. 31 32 885.

Of the known developer substances, those which may be employed as components of the hair coloring compositions according to the present invention include, by way of example, 1,4-diaminobenzene, 2,5-diaminotoluene, 2,5-diaminoanisol, 2,5-diaminobenzyle alcohol, 3-methyl-4-aminophenol and 4-aminophenol.

The coupler substances of formula I are generally employed in about molar amounts, relative to the employed developer substances. Even when the equimolar amount proves to be expedient, it is still not disadvantageous for the coupler substance to be employed in a certain excess or deficiency. Moreover, it is not necessary that the developer components and the coupler components represent unitary products, i.e., frequently, not only can the developer component represent a mixture of known developer substances, but also the coupler component can represent a mixture of coupler according to the present invention with known coupler substances.

The total amount of developer substance-coupler substance-combination contained in the herein described hair coloring compositions should be between about 0.1 and 5.0 percent by weight, preferably 0.5 to 3.0 percent by weight.

Moreover, the hair coloring composition according to the present invention can additionally contain other color components, for example, 6-amino-2-methylphenol, 2-amino-5-methylphenol and 2-amino-5-ethoxyphenol as well as, moreover, customary direct-drawing dyes, for example triphenylmethane dyes such as Diamond Fuchsine (C.I. 42 510) and Leather Ruby HF (C.I. 42 520), aromatic nitro dyes such as 2-nitro-1,4-diaminobenzene, azo dyes such as Acid Brown 4 (C.I. 14 805) and Acid Blue 135 (C.I. 13 385), anthraquionone dyes such as Disperse Red 15 (C.I. 60 710) and Disperse Violet 1 (C.I. 61 100), moreover, 1,4,5,8-tetraaminoanthraquinone and 1,4-diaminoanthraquinone.

Obviously, the coupler and developer substances, as well as even other color components, insofar as bases are concerned, can be employed in the form of physiologically compatible acid addition salts, such as for example hydrochloride or sulphate, or—insofar as they possess aromatic OH-groups—in the form of the salt with bases, for example, as alkaliphenolate.

In other respects, the still further customary cosmetic additives, for example antioxidants such as ascorbic acid or sodium sulphite, perfume oils, complex formers, wetting agents, emulsifiers, thickeners, care substances and the like, can be provided in the hair coloring compositions.

The preparations can be, for example, in the form of a solution, particularly an aqueous, or aqueous-alcoholic solution. The particularly preferred form of preparations are, however, a cream, a gel or an emulsion.

Their composition represents a mixture of the dye components with the additives customary for such preparations.

Customary additives in solutions, creams, emulsions or gels are, for example, solvents such as water, lower aliphatic alcohols, for example ethanol, propanol and isopropanol, as well as multi-valent alcohols, such as ethylene glycol, 1,2-propylene glycol and glycerine, moreover wetting agents or emulsifiers from the classes of anionic, cationic, amphoteric or non-ionogenic surface-active substances, such as fatty alcohol sulphate, alkylsulfonate, alkylbenzene sulfonate, alkyltrimethylammonium salts, alkylbetaine, oxethylated fatty alcohols, oxethylated nonylphenols, fatty acid alkanolamides, oxethylated fatty acid ester, moreover thickeners such as higher fatty alcohols, Bentonite, starch, polyacrylic acid, cellulose derivatives, alginates, vaseline ®, paraffin oil and fatty acids, as well as, moreover, care substances such as lanolin derivatives, cholesterin, pantothenic acid and betaine. The mentioned components are employed in amounts customary for such purposes, for example, the wetting agents and emulsifiers in concentrations from about 0.5 up to 30 percent by weight, whereas the thickeners can be contained in amounts from about 0.1 up to 25 percent by weight in the preparations.

Indeed according to composition, the hair coloring means according to the present invention can react weakly acid, neutral or alkaline. In particular, they display a pH value in the alkaline range between 8.0 and 11.5, whereby an adjustment preferably follows by means of ammonia. However, also organic amines, for example monoethanol amine and triethanol amine, or even inorganic bases, such as sodium hydroxide and potassium hydroxide, can be employed.

For the employment for oxidative dyeing of hair, one mixes the above described hair coloring compositions directly before use, with an oxidation agent, and then a sufficient amount for the hair treatment is applied to the hair, indeed depending upon the fullness of hair, generally, however, between 60 and 200 g. of this mixture. Coming into consideration as oxidation agents for the development of the hair coloration are mainly hydrogen peroxide or its addition compounds with urea, melamine, or sodium borate, in the form of 3-12%, preferably 6%, aqueous solutions. If a 6% hydrogen peroxide solution is employed as oxidation agent, the weight ratio between hair coloring composition and oxidation agent amounts to between 5:1 and 1:2, preferably, however, 1:1. Greater amounts of oxidation agent are employed mainly with higher dye concentrations in the hair coloring composition, or when simultaneously a stronger bleaching of the hair is considered. One allows the mixture to remain and work itself into the hair about 10–45 minutes, preferably 30 minutes, at a temperature between 15° and 50° C. Then, the hair is rinsed with water and dried. If necessary, at the conclusion of this rinsing, the hair can be washed with a shampoo and eventually after-rinsed with a weak organic acid, such as for example, citric or tartaric acid. Subsequently, the hair is dried.

The 3-amino-5-hydroxypyridine derivatives of formula I contained in the hair coloring compositions according to the present invention are new, and therefore likewise within the subject of this application. Their preparation is illustrated by way of the following reaction scheme.

For the preparation, one proceeds from the known compounds of general formula VII. The manufacture of 2,6-dimethoxy-3-nitropyridine is described, for example, by C. D. Johnson et al, J. Chem. Soc. (B), 1967, pp. 1204–1210. The 2,6-(2'-hydroxyethyloxy)-3-nitropyridine and the 2,6-diethoxy-3-nitropyridine can also be obtained from 2,6-dichlor-3-nitropyridine by means of nucleophilic exchange of the chlorine with the alcoholate of the ethylene glycol or of the ethyl alcohol. By means of successive catalytic reduction (Stage 1), acetylation (Stage 2) and nitrification (Stage 3), the 3-acetylaminonitropyridine derivative IV is obtained.

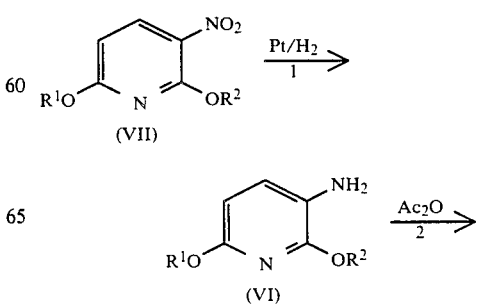

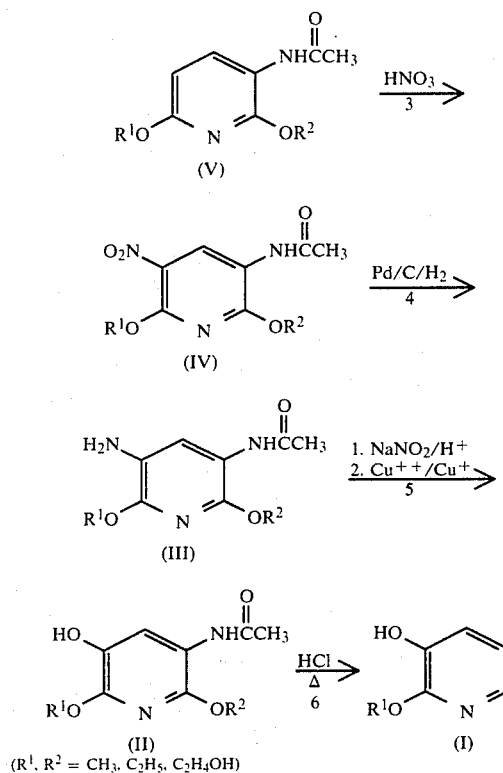

(R¹, R² = CH₃, C₂H₅, C₂H₄OH)

By means of repeated catalytic hydrogenation (Stage 4), one obtains the 5-aminopyridine derivative III, which is then converted into the 5-hydroxypyridine derivative II (Stage 5) by means of diazonium salt concentration according to T. Cohen et al, J. Org. Chem. Vol. 42, No. 12, (1977), pp. 2053–58. Upon subsequent heating with dilute hydrochloric acid (Stage 6) the compounds of formula II saponify, and the compounds of formula I according to the present invention precipitate in the form of the hydrochlorides.

With regard to color possibilities, the hair coloring compositions according to the present invention, indeed accordto type and composition of the color components, offer a broad palette of the most various color nuances, which stretch from red and red-browns to blonds and gold tones. Herewith, the color tones distinguish by their particular color intensity and fastness to light.

The previously mentioned pyridine derivatives promote, as coupler substances in combination with the developer substances, 1,4-diaminobenzene and its derivatives, very intensive red to red-brown tones. In combination with p-aminophenol, orange colored tones are obtained.

Coupling components which, with the customary developer substances, promote such color tones, are very desirable since they make it possible to produce even so-called mod red and brown nuances within the realm of oxidative hair dyes without having to employ the aromatic nitro-dyes.

Of further advantage is the combination possibility of the red couplers according to the present invention with the known blue couplers of the pyridine series, whereby by means of the structural similarity, also comparable water solubilities and diffusion characteristics are obtained. This facilitates the production of hair dyes which provide uniform coloration even to injured hair.

However, the advance obtained with regard to toxicological and dermatological viewpoints by means of the employment of the 3-amino-5-hydroxypyridine derivatives of formula I in the present hair dyeing compositions is of particular significance.

Thus, for example, the coupler substance according to the present invention 3-amino-5-hydroxy-2,6-dimethoxy-pyridine proves in the Amea-Test with Salmonella-typhimurium stocks TA 1535, TA 1537, TA 1538, TA 98 and TA 100 not only in the presence but also in the absence of an activation system, no mutagenic activity.

The following Examples more clearly illustrate the subject of the present invention.

COLOR EXAMPLES

EXAMPLE 1

Hair dyeing means in gel form

| | |
|---|---|
| 0.65 g | 3-amino-5-hydroxy-2,6-dimethoxypyridine hydrochloride |
| 0.70 g | 2,5-diaminotoluene sulfate |
| 0.30 g | ascorbic acid |
| 1.00 g | hydroxyethylcellulose, with viscosity |
| 5.00 g | laurylalcohol-diglycolethersulfate-sodium salt (28% aqueous solution) |
| 10.00 g | ammonia, 25% |
| 82.35 g | water |
| 100.00 g | |

50 g of the above hair coloring composition are mixed briefly before use with 50 g. hydrogen peroxide solution (6%), and the mixture is subsequently applied to white, human hair. After a working-in period of 30 minutes at about 40° C., the hair is rinsed with water and dried. The hair is colored in a copper-brown tone.

EXAMPLE 2

Hair coloring composition in cream form

| | |
|---|---|
| 0.70 g | 3-amino-5-hydroxy-2,6-di-(2'-hydroxy-ethyloxy)-pyridine-hydrochloride |
| 0.30 g | 4-aminophenol |
| 0.30 g | sodium sulfite, water free |
| 3.50 g | lauryl alcohol-diglycolethersulfate-sodium salt (28% aqueous solution) |
| 15.00 g | cetyl alcohol |
| 3.00 g | ammonia, 25% |
| 77.20 | water |
| 100.00 g | |

50 g of this hair coloring composition are mixed briefly before use with 50 g hydrogen peroxide solution (6%). The mixture is subsequently applied to white human hair. After a working-in period of 30 minutes at 40° C., the hair is initially rinsed with water, and then with a dilute citric acid solution, and subsequently dried. The hair is colored an orange colored tone.

EXAMPLE 3

Hair coloring composition in gel form

| | |
|---|---|
| 0.10 g | 3-amino-5-hydroxy-2,6-dimethoxypyridine-hydrochloride |
| 0.30 g | 1,4-diaminobenzene |
| 0.20 g | resorcin |

-continued

| | |
|---|---|
| 0.30 g | ascorbic acid |
| 15.00 g | oleic acid |
| 7.00 g | isopropanol |
| 10.00 g | ammonia, 25% |
| 67.10 g | water |
| 100.00 g | |

Briefly before use, 50 g of this hair coloring composition are mixed with 50 g hydrogen peroxide solution (6%), after which the mixture is applied to white human hair. Following a working-in period of 30 minutes at 40° C., the hair is rinsed with water and dried. The hair is colored a reddish-medium blond color tone.

EXAMPLE 4

Hair coloring composition in cream form

| | |
|---|---|
| 0.20 g | 3-amino-5-hydroxy-2,6-dimethoxypyridine-hydrochloride |
| 0.20 g | 3,5-diamino-2,6-dimethoxypyridine-dihydrochloride |
| 0.40 g | resorcin |
| 1.20 g | 2,5-diaminotoluenesulfate |
| 0.30 g | ascorbic acid |
| 13.50 g | cetylstearyl alcohol |
| 1.50 g | sodiumcetylstearylsulfate |
| 10.00 | paraffin oil |
| 5.00 g | wool fat |
| 4.00 g | ammonia, 25% |
| 63.70 g | water |
| 100.00 g | |

50 g of the above hair coloring composition are mixed with 50 g hydrogen peroxide solution (6%) briefly before use, and then applied to blond human hair. Following a working-in period of 30 minutes at 40° C., the hair is rinsed initially with water and then with a dilute citric acid solution. Finally, the hair is dried. The hair is colored black.

PRODUCTION EXAMPLE

EXAMPLE 5

Production of 3-amino-5-hydroxy-2,6-dimethoxypyridine-hydrochloride

Stage 1: Catalytic hydrogenation of 3-nitro-2,6-dimethoxypyridine- 54.9 g (0.30 mol) of the nitro compound are hydrogenated at normal pressure and room temperature on platinum as a catalyst. After conclusion of the hydrogen reception, the catalyst is filtered off, the solution is reacted up to an acid reaction with concentrated hydrochloric acid, and then compressed in a vacuum.

42.14 g pure 3-amino-2,6-dimethoxypyridine-hydrochloride crystallize out. A further 8.20 g of the compound are isolated from the mother liquor. Total yield: 50.3 g (88% of theoretical amount), colorless to light red-violet crystals, melting point 207°–208° C. (decomposition).

Stages 2 & 3: Acetylation of 3-amino-2,6-dimethoxypyridine-hydrochloride and nitrification into 3-acetylamino-5-nitro-2,6-dimethoxypyridine.

25.75 g (0.135 mol) 3-amino-2,6-dimethoxy-pyridine-hydrochloride are stirred in 30 ml acetic acid anhydride for 1 hour at 80° C. under exclusion of moisture. The crystals are thereby dissolved. The acetic acid anhydride is distilled off in a vacuum and the residue is withdrawn in 30 ml glacial acetic acid.

For the nitration a mixture of 90 ml nitric acid (65%) and 57 ml water are provided and cooled down to 0° C. Under intense stirring, the solution of the acetyl compound is allowed to flow in during a period of 20 minutes. Therewith the temperature is maintained at 0°–5° C. by means of an ice bath.

The nitro compound precipitates in the form of fine yellow crystals. One then stirs for 10 minutes, followed by dilution with 100 ml. ice water, and filtration with after-washing with water. The nitro compound is thin layer chromatographically pure, and melts at 209°–210° C.

Yield: 21.1 g. (65% of theoretical amount, relative to the amino compound.)

The above, directly converted acetyl amino compound can also be isolated. It crystallizes after evaporation of the acetic acid anhydride and allowing to stand of the oil. One obtains colorless crystals, which can be filtered off by means of after-washing with ether.

Stage 4: Catalytic reduction of the 3-acetylamino-5-nitro-2,6-dimethoxypyridine.

18.0 g (0.075 mol) nitro compound are suspended in 200 ml methanol, and then hydrogenated at normal pressure and a temperature 30°–40° C. on palladium/activated coal (5%). The hydrogen reception is completed after 1½ hours. The catalyst is filtered off and then the solvent evaporated in a vacuum. The residue crystallizes in the form of light blue crystals of melting point 179° C. (decomposition).

The yield amounts to 14.55 g (92.4% of theoretical amount.)

Stages 5–6: Diazonium salt concentration and saponification of the acetylamino-group.

14.5 g (0.069 mol) of the amino compound from Stage 4 are dissolved in 100 ml of 2-normal sulfuric acid (0.2 equivalents) at 0° C., and then, within 10 minutes, diazotized by means of addition of 4.75 g (0.069 mol) sodium nitrite, dissolved in 20 ml water. The reaction mixture is stirred an additional 10 minutes at 0° C. Subsequently, the diazonium salt solution is run into a solution of 350 g copper nitrate-trihydrate in 3 l water. Under intense stirring, 9.85 g (0.069 mol) copper-(I)-oxide are added at one time. The mixture foams violently, with gas development complete after 15 minutes. The solution is extracted several times with methylene chloride, the combined methylene chloride phases are then dried across sodium sulfate and the solvent is evaporated in a vacuum. The black residue (8 g) is heated, with stirring for 1 hour with 150 ml semi-concentrated hydrochloric acid to 80°–90° C. The solution is initially blue, then reddish. After compression of the reaction mixture, 2.34 g of 3-amino-5-hydroxy-2,6-dimethoxypyridine-hydrochloride crystallize out in fine needles of melting point 238° C. (decomposition). The mother liquor is compressed in a rotation evaporator, after which the residue is withdrawn in methanol and cooked with animal charcoal. After filtration and the addition of ethyl acetate, a further 2.00 g of the compound crystallizes out.

Yield: 4.34 g (31% of theoretical amount relative to the employed 3-amino-5-acetylamino-2,6-dimethoxypyridine).

It will be understood that each of the elements described above, or two or more together, may also find a useful application in other types of compositions differing from the types described above.

While the invention has been illustrated and described as embodied in new 3-amino-5-hydroxypyridine derivatives and hair coloring compositions containing the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. 3-amino-5-hydroxypyridine derivatives of the general formula I

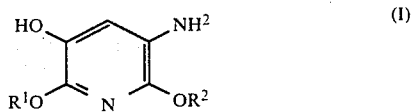

wherein $R^1$ and $R^2$ are the same or different and are each $CH_3$, $C_2H_5$ or $C_2H_4OH$ and its physiologically compatible salt with an organic or inorganic acid.

2. 3-amino-5-hydroxy-2,6-dimethoxypyridine.

3. 3-amino-5-hydroxy-2,6-di-(2'-hydroxyethyloxy)-pyridine.

4. Composition for the oxidative dyeing of hair, containing a developer substance-coupler substance combination, including as coupler substance a 3-amino-5-hydroxyprydine derivative of the general formula I

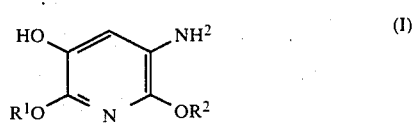

wherein $R^1$ and $R^2$ are the same or different and are each $CH_3$, $C_2H_5$ or $C_2H_4OH$ or a physiologically compatible salt thereof with an organic or inorganic acid.

5. The composition according to claim 4, wherein said coupler substance of general formula I is contained in amount from 0.01 up to 3.0 percent by weight.

6. The composition according to claim 5, wherein said concentration is between 0.1 and 2.0 percent by weight.

7. The composition according to claim 5, containing as coupler substance 3-amino-5-hydroxy-2,6-dimethoxypyridine.

8. The composition according to claim 4, further comprising a known coupler substance selected from the group consisting of resorcin, 4-chlororesorcin, 2-methylresorcin, 4,6-dichlororesorcin, 2,4-diaminobenzylalcohol, 2-amino-4-(2'-hydroxyethylamino)-anisol, 2,4-diaminophenyl-ethanol, 2,4-diaminophenoxyethanol, 2,4-diaminoanisol, 2,4-diaminophenetol, 3,5-diamino-2,6-dimethoxypyridine, 3,5-diamino-2,6-di(2'-hydroxyethyloxy)-pyridine, 1,5-dihydroxytetralin, 5-amino-2-methylphenol, 4-hydroxy-1,2-methylenedioxybenzene, 4-amino-1,2-methylene-dioxybenzene and 4-(2'-hydroxyethylamino)-1,2-methylenedioxybenzene.

9. The composition according to claim 4, wherein said developer substance is selected from the group consisting of 1,4-diaminobenzene, 2,5-diamonotoluene, 2,5-diaminoanisol, 2,5-diaminobenzylalcohol, 3-methyl-4-aminophenol and 4-aminophenol.

10. The composition according to claim 4, further containing as a color component a compound selected from the group consisting of 6-amino-2-methylphenol, 2-amino-5-methylphenol, 2-amino-5-ethoxyphenol, Diamond Fuchsine (C.I. 42 510), Leather Ruby HF (C.I. 42 520), 2-nitro-1,4-diaminobenzene, 2-amino-4-nitrophenol, 2-amino-5-nitrophenol, Acid Brown 4 (C.I. 14 805), Acid Blue 135 (C.I. 13 385), Disperse Red 15 (C.I. 60 710), Disperse Violet 1 (C.I. 61 100), 1,4,5,8-tetraaminoanthraquinone and 1,4-diaminoanthraquinone.

11. Aqueous composition for the oxidative dyeing of hair, containing 0.1 to 5.0% by weight of a developer substance-coupler substance combination, including as coupler substance a 3-amino-5-hydroxypyridine derivative of the general formula I

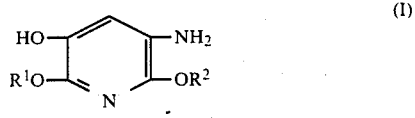

wherein $R^1$ and $R^2$ are the same or different and are each $CH_3$, $C_2H_5$ or $C_2H_4OH$ or a physiologically compatible salt thereof with an organic or inorganic acid.

12. The composition according to claim 11, wherein the total amount of coupler substance-developer substance combination is between 0.5 and 3.0 percent by weight.

* * * * *